(12) United States Patent
Hamauzu (10) Patent No.: US 11,389,132 B2
(45) Date of Patent: Jul. 19, 2022

(54) RADIOGRAPHIC IMAGE PROCESSING APPARATUS, RADIOGRAPHIC IMAGE PROCESSING METHOD, AND RADIOGRAPHIC IMAGE PROCESSING PROGRAM

(71) Applicant: FUJIFILM CORPORATION, Tokyo (JP)

(72) Inventor: Shin Hamauzu, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 261 days.

(21) Appl. No.: 16/916,170

(22) Filed: Jun. 30, 2020

(65) Prior Publication Data

US 2021/0015440 A1    Jan. 21, 2021

(30) Foreign Application Priority Data

Jul. 16, 2019  (JP) .............................. JP2019-131227

(51) Int. Cl.
  *A61B 6/00*       (2006.01)
  *H04N 5/32*       (2006.01)

(52) U.S. Cl.
  CPC .......... *A61B 6/5217* (2013.01); *A61B 6/5205* (2013.01); *H04N 5/32* (2013.01)

(58) Field of Classification Search
  CPC ... A61B 5/0066; A61B 5/0084; A61B 5/0073; A61B 34/10; A61B 90/37; A51B 5/00; G01N 21/4795; G01N 2223/419; G01N 23/046; G01N 2021/4719; G01B 34/10; G01B 9/02091; G06T 7/0014; G06T 2207/20221; G06T 2207/20212
  See application file for complete search history.

(56) References Cited

FOREIGN PATENT DOCUMENTS

JP    2018-068863 A    5/2018
WO   WO-2019132614 A1 * 7/2019 ............. A61B 34/10

* cited by examiner

*Primary Examiner* — Don K Wong
(74) *Attorney, Agent, or Firm* — Solaris Intellectual Property Group, PLLC (57) ABSTRACT

The radiographic image processing apparatus comprises a detection unit including a discriminator that has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image. The discriminator discriminates the surgical tool region in the input radiographic image to detect the surgical tool region.

9 Claims, 6 Drawing Sheets

RADIOGRAPHIC IMAGE PROCESSING APPARATUS, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2019-131227 filed on Jul. 16, 2019. The above application is hereby expressly incorporated by reference, in its entirety, into the present application.

BACKGROUND

Technical Field

The present disclosure relates to a radiographic image processing apparatus, a radiographic image processing method, and a radiographic image processing program.

Related Art

Various surgical tools, such as gauze to suppress bleeding, a thread and a needle for sewing up a wound, a scalpel and scissors for incision, a drain for draining blood, and forceps for opening incision, are used in a case in which a surgical operation is performed for a patient. The surgical tools may cause serious complications in a case in which they remain in the body of the patient after surgery. Therefore, it is necessary to check that no surgical tools remain in the body of the patient after surgery.

Therefore, a method has been proposed which prepares a discriminator that has trained the characteristics of a gauze image and inputs an image acquired by capturing a surgical field with a camera to the discriminator to discriminate whether or not gauze is present (see JP2018-068863A).

However, since gauze is stained with blood, it is difficult to find gauze in an image acquired by a camera even in a case in which a discriminator is used. In contrast, it is considered that a radiographic image of the patient is acquired after surgery and is observed to check whether or not a surgical tool remains in the body of the patient. However, after long surgery, both the operator and the nurse are tired. Therefore, there is a problem that the possibility of missing the remaining surgical tools is high. In addition, since the radiographic image which includes a surgical tool, such as gauze, and is necessary for training the discriminator is extremely rare, it is difficult to collect a large number of radiographic images for training the discriminator.

SUMMARY OF THE INVENTION

The present disclosure has been made in view of the above-mentioned problems and an object of the present disclosure is to provide a technique that can reliably prevent a surgical tool from remaining in the body of a patient after surgery.

According to the present disclosure, there is provided a radiographic image processing apparatus comprising a detection unit including a discriminator that has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image. The detection unit discriminates the surgical tool region in the input radiographic image using the discriminator to detect the surgical tool region.

The radiographic image processing apparatus according to the present disclosure may further comprise a display control unit that displays the radiographic image on a display unit such that the surgical tool region detected in the radiographic image is highlighted.

The radiographic image processing apparatus according to the present disclosure may further comprise a combination unit that combines the first radiographic image and the second radiographic image using a combination parameter corresponding to characteristics of the first radiographic image and the surgical tool to generate the composite image.

In this case, the combination unit may set the combination parameter according to at least one of radiation absorptivity of the surgical tool, a degree of scattering of radiation in the first radiographic image, beam hardening in the first radiographic image, or noise corresponding to imaging conditions of the first radiographic image.

In the radiographic image processing apparatus according to the present disclosure, the surgical tool may include at least one of gauze, a scalpel, scissors, a drain, a needle, a thread, or forceps.

Further, in the radiographic image processing apparatus according to the present disclosure, at least a portion of the gauze may include a radiation absorbing thread.

The term "at least a portion" means that not only a portion of the gauze but also the entire gauze may include the radiation absorbing thread.

Further, the radiographic image processing apparatus according to the present disclosure may further comprise a learning unit that trains the discriminator, using a learning image consisting of the composite image and correct answer data in which a position of the surgical tool in the composite image is specified.

According to the present disclosure, there is provided a radiographic image processing method performed in a radiographic image processing apparatus comprising a detection unit including a discriminator that has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image. The method comprises allowing the detection unit to discriminate the surgical tool region in the input radiographic image using the discriminator to detect the surgical tool region.

In addition, a program that causes a computer to perform the radiographic image processing method according the present disclosure may be provided.

Another radiographic image processing apparatus according to the present disclosure comprises a memory that stores commands to be executed by a computer and a processor that is configured to execute the stored commands. The processor functions as a detection unit including a discriminator that has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image, and performs a process of discriminating the surgical tool region in the input radiographic image to detect the surgical tool region.

According to the present disclosure, it is possible to reliably prevent a surgical tool from remaining in the body of a patient after surgery.

DETAILED DESCRIPTION

Figure 1:
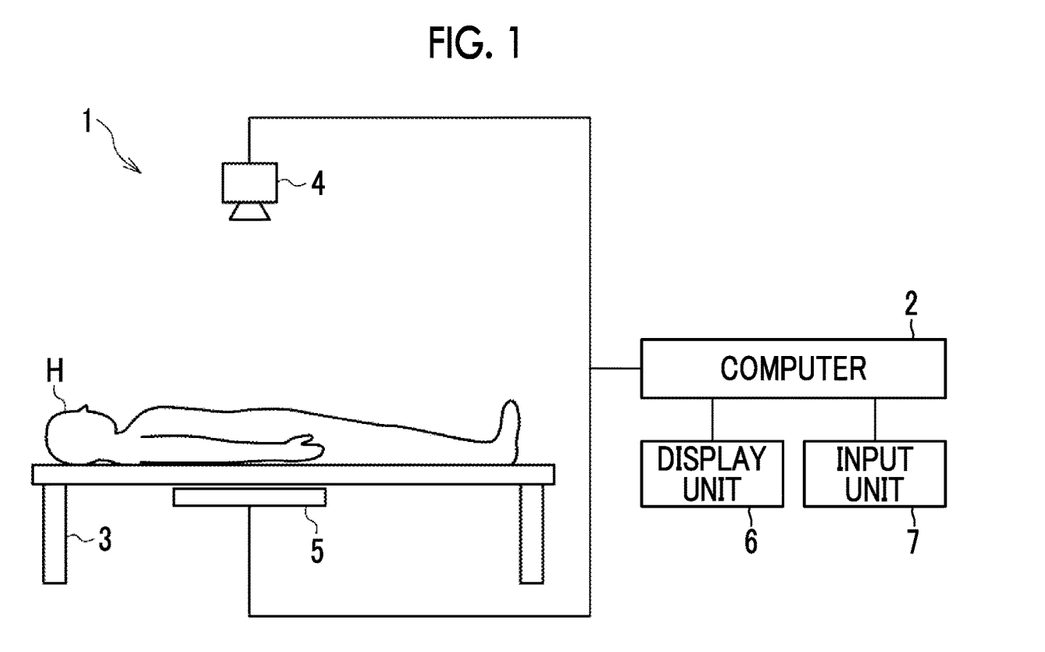
FIG. 1 is a block diagram schematically illustrating a configuration of a radiography system to which a radiographic image processing apparatus according to an embodiment of the present disclosure is applied.

Hereinafter, embodiments of the present disclosure will be described with reference to the drawings. FIG. 1 is a block diagram schematically illustrating a configuration of a radiography system to which a radiographic image processing apparatus according to an embodiment of the present disclosure is applied. As illustrated in FIG. 1, the radiography system according to this embodiment acquires a radiographic image of a subject H as a patient after a surgical operation and detects a surgical tool included in the radiographic image. The radiography system according to this embodiment comprises an imaging apparatus 1 and a computer 2 which is the radiographic image processing apparatus according to this embodiment.

The imaging apparatus 1 irradiates a radiation detector 5 with radiation which has been emitted from a radiation source 4, such as an X-ray source, and transmitted through the subject H to acquire a radiographic image G0 of the subject H that lies supine on an operating table 3. The radiographic image G0 is input to the computer 2 which is the radiographic image processing apparatus.

The radiation detector 5 can repeatedly perform the recording and reading of a radiographic image and may be a so-called direct-type radiation detector that directly receives the emitted radiation and generates charge or a so-called indirect-type radiation detector that converts radiation into visible light and then converts the visible light into a charge signal. As a method for reading a radiographic image signal, it is desirable to use a so-called thin film transistor (TFT) reading method which turns on and off a TFT switch to read a radiographic image signal or a so-called optical reading method which emits reading light to read a radiographic image signal. However, the present disclosure is not limited thereto and other methods may be used.

A display unit 6 and an input unit 7 are connected to the computer 2. The display unit 6 is a display such as a cathode ray tube (CRT) or a liquid crystal display and assists the input of a radiographic image acquired by imaging and various kinds of data necessary for processes performed by the computer 2. The input unit 7 consists of, for example, a keyboard, a mouse, or a touch panel.

A radiographic image processing program according to this embodiment is installed in the computer 2. In this embodiment, the computer may be a workstation or a personal computer that is directly operated by an operator or a server computer that is connected to the computer through a network. The radiographic image processing program is stored in a storage device of the server computer connected to the network or a network storage so as to be accessed from the outside and is downloaded and installed in the computer on demand. Alternatively, the radiographic image processing program is recorded on a recording medium such as a digital versatile disc (DVD) or a compact disc read only memory (CD-ROM), is distributed, and is installed in the computer from the recording medium.

Figure 2:
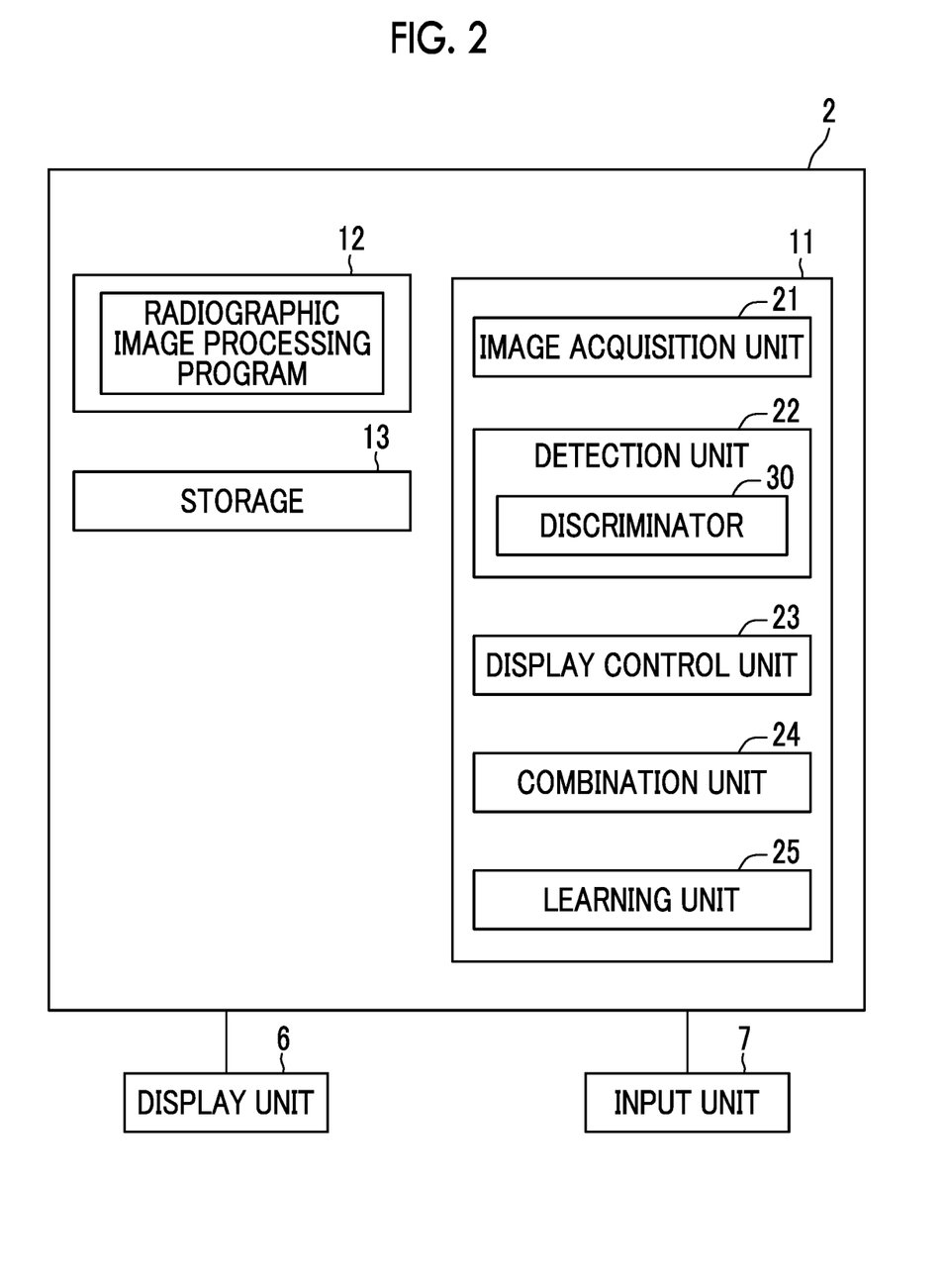
FIG. 2 is a diagram schematically illustrating a configuration of the radiographic image processing apparatus according to this embodiment.

FIG. 2 is a diagram schematically illustrating the configuration of the radiographic image processing apparatus implemented by installing, for example, the radiographic image processing program in the computer 2 in this embodiment. As illustrated in FIG. 2, the radiographic image processing apparatus comprises a central processing unit (CPU) 11, a memory 12, and a storage 13 as a standard computer configuration.

The storage 13 is a storage device, such as a hard disk or a solid state drive (SSD), and stores various kinds of information including an imaging program for driving each unit of the imaging apparatus 1 and the radiographic image processing program. In addition, the radiographic image acquired by imaging is stored in the storage 13.

The memory 12 temporarily stores, for example, the radiographic image processing program stored in the storage 13 in order to cause the CPU 11 to perform various processes. The radiographic image processing program defines the following processes as the processes to be performed by the CPU 11: an image acquisition process that irradiates the radiation detector 5 with the radiation, which has been emitted from the radiation source 4 and then transmitted through the subject H, to acquire the radiographic image G0 and acquires a first radiographic image G1 including the subject H and a second radiographic image G2 indicating a surgical tool which are used to generate a composite image; a detection process that detects the surgical tool included in the input radiographic image G0; a display control process that displays the radiographic image G0 from which the surgical tool has been detected on the display unit 6; a combination process that combines the first radiographic image G1 and the second radiographic image G2 indicating the surgical tool, which have been acquired in the image acquisition process and are used to generate the composite image, to generate a composite image C0; and a learning process that trains a discriminator for discriminating a surgical tool region in the input radiographic image on the basis of training data consisting of the composite image C0 and correct answer data indicating the surgical tool region in the composite image C0.

The CPU 11 performs the above-mentioned processes according to the radiographic image processing program such that the computer 2 functions as an image acquisition unit 21, a detection unit 22, a display control unit 23, a combination unit 24, and a learning unit 25.

The image acquisition unit 21 drives the radiation source 4 to irradiate the subject H that has undergone surgery with radiation and detects the radiation transmitted through the subject H using the radiation detector 5 to acquires the radiographic image G0. In this case, the image acquisition unit 21 sets imaging conditions, such as the type of target and filter used in the radiation source 4, an imaging dose, a tube voltage, and an SID. Further, the image acquisition unit 21 acquires the first radiographic image G1 including any subject H in order to generate the composite image C0 which will be described below. The subject H whose first radiographic image G1 is acquired does not include the surgical tool. In addition, the image acquisition unit 21 acquires the second radiographic image G2 indicating the surgical tool. The radiographic image processing apparatus according to this embodiment may acquire the radiographic images G0, G1, and G2 using a program different from the radiographic image processing program and store the acquired radiographic images G0, G1, and G2 in the storage 13. In this case, the image acquisition unit 21 reads the radiographic images G0, G1, and G2 stored in the storage 13 and acquires the radiographic images G0, G1, and G2. In this embodiment, it is assumed that gauze is used as the surgical tool.

Figure 3:
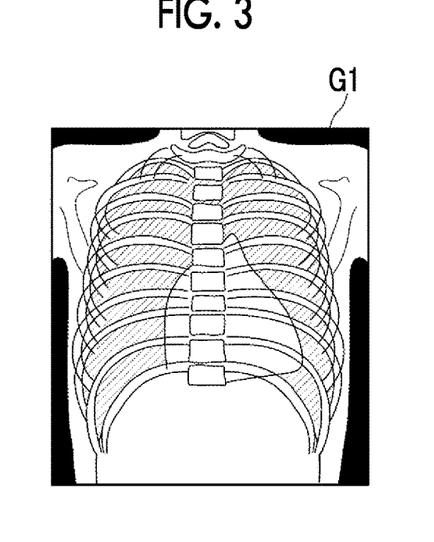
FIG. 3 is a diagram illustrating a first radiographic image.

Next, a process performed by the combination unit 24 will be described. The combination unit 24 combines the first radiographic image G1 and the second radiographic image G2 indicating the surgical tool, which are used to generate the composite image C0, to generate the composite image C0. FIG. 3 is a diagram illustrating the first radiographic image G1 for generating the composite image. In this embodiment, it is assumed that the first radiographic image G1 including the chest and abdomen of the human body is acquired as illustrated in FIG. 3.

Figure 4:
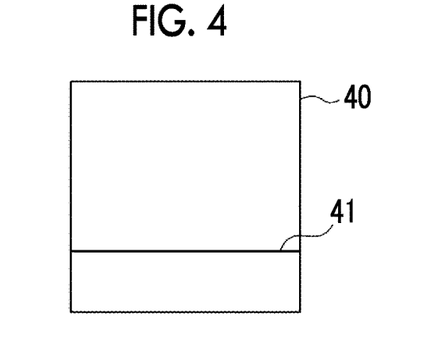
FIG. 4 is a diagram illustrating gauze.

FIG. 4 is a diagram illustrating gauze. As illustrated in FIG. 4, gauze 40 is a plain-woven cotton fabric and a radiation absorbing thread 41 is woven in a portion of the gauze 40. Cotton yarn transmits radiation and the radiation absorbing thread 41 absorbs radiation. Therefore, the radiographic image of the gauze 40 includes only the linear radiation absorbing thread 41. Here, during surgery, the gauze 40 is rolled and inserted into the human body in order to absorb blood. In this embodiment, it is assumed that the second radiographic image G2 is acquired by appropriately rolling the gauze and capturing the image of the gauze in order to match with the aspect in which the gauze 40 is actually used. The gauze 40 may consist of only the radiation absorbing thread 41.

Figure 5:
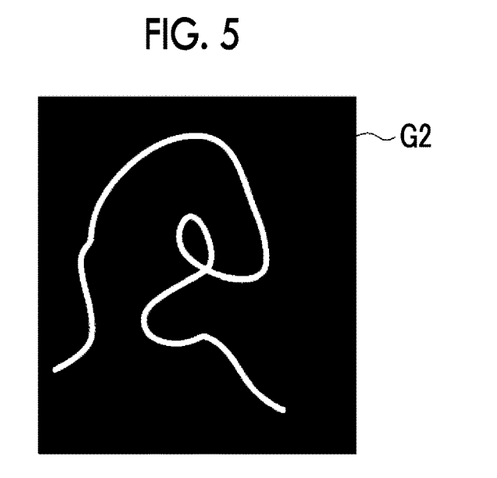
FIG. 5 is a diagram illustrating a second radiographic image.

FIG. 5 is a diagram illustrating the second radiographic image G2. A region of the radiation absorbing thread 41 in the second radiographic image G2 corresponds to the amount of attenuation of radiation by the radiation absorbing thread 41. Therefore, in the second radiographic image G2, the radiation absorbing thread 41 included in the gauze 40 has high brightness (low density).

The combination unit 24 combines the first radiographic image G1 and the second radiographic image G2 to generate the composite image C0. The combination unit 24 combines the first radiographic image G1 and the second radiographic image G2 with combination parameters corresponding to the characteristics of the surgical tool (the gauze 40 in this embodiment) to generate the composite image C0. The combination unit 24 sets the combination parameters according to at least one of the radiation absorptivity of the surgical tool (the gauze 40 in this embodiment), the degree of scattering of radiation by the surgical tool, beam hardening in the first radiographic image G1, or noise corresponding to the imaging conditions of the first radiographic image G1.

Figure 6:
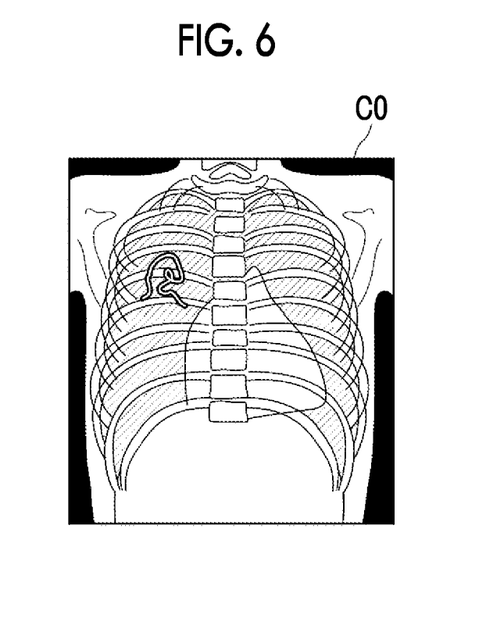
FIG. 6 is a diagram illustrating a composite image.

In this embodiment, for example, it is assumed that the composite image C0 is generated by the following Expression (1). That is, in pixels (x, y) of a region of the first radiographic image G1 which is combined with the second radiographic image G2, a pixel value G2(x, y) of the second radiographic image G2 weighted by a weight coefficient w1 is subtracted from a pixel value G1(x, y) of the first radiographic image G1 to derive a pixel value C0(x, y) of the composite image C0. In addition, the weight coefficient w1 has a value that is equal to or greater than 0 and equal to less than 1. The weight coefficient w1 is included in the combination parameters according to this embodiment. The combination unit 24 sets the coordinate positions of the upper left corner and the lower right corner of the combination position of the second radiographic image G2 in the first radiographic image G1 and enlarges or reduces the second radiographic image G2 such that the upper left corner and the lower right corner of the second radiographic image G2 are matched with the set coordinate positions to combine the first radiographic image G1 and the second radiographic image G2. FIG. 6 is a diagram illustrating the composite image. As illustrated in FIG. 6, in the composite image C0, the radiation absorbing thread 41 of the gauze 40 is included in the right lung of the subject.

$$C0(x,y)=G1(x,y)-w1 \cdot G2(x,y) \quad (1)$$

Here, as the radiation absorptivity of the surgical tool increases, the contrast of the surgical tool in the second radiographic image G2 increases. For example, in a case in which the surgical tool is a metal tool, such as scissors or a scalpel, the contrast of the surgical tool is higher than the contrast of the radiation absorbing thread 41 in the second radiographic image G2. Therefore, in a case in which the first radiographic image G1 and the second radiographic image G2 are added, the weight coefficient w1 for the second radiographic image G2 is increased such that the contrast of the surgical tool in the composite image C0 is not too high.

Further, the contrast of the radiographic image is reduced due to the scattering of radiation. The influence of the scattering of radiation becomes larger as the body thickness of the subject H becomes larger. Further, as the body thickness of the subject H becomes larger, the density of a subject region included in the first radiographic image G1 becomes lower. Therefore, the combination unit 24 derives the average value of the density of the subject region included in the first radiographic image G1, reduces the weight coefficient w1 such that a density difference between the first radiographic image G1 and the second radiographic image G2 becomes smaller as the average value become smaller, that is, the body thickness of the subject H becomes larger, and generates the composite image C0.

Here, beam hardening occurs in which, as the tube voltage applied to the radiation source 4 becomes higher and the energy of radiation becomes higher, a lower-energy component of the radiation is absorbed by the subject H and the energy of the radiation becomes higher while the radiation is transmitted through the subject H. In a case in which the beam hardening occurs, the contrast of the radiographic image decreases. Further, the increase in the energy of radiation due to the beam hardening becomes more significant as the body thickness of the subject H becomes larger. Further, as the body thickness of the subject H becomes larger, the density of a subject region included in the first radiographic image G1 becomes lower. Therefore, the combination unit 24 derives the average value of the density of the subject region included in the first radiographic image G1, reduces the weight coefficient w1 such that a density difference between the first radiographic image G1 and the second radiographic image G2 becomes smaller as the average value become smaller, that is, the body thickness of the subject H becomes larger, and generates the composite image C0.

In addition, in a case in which the radiation dose in the imaging conditions is reduced, the amount of noise included in the first radiographic image G1 increases. Therefore, in a case in which the radiation dose is small, the combination unit 24 adds noise N(x, y) corresponding to the radiation dose to Expression (1) to generate the composite image C0, as illustrated in the following Expression (2). In this case, the weight coefficient w1 may be a predetermined value or may be set according to at least one of the radiation absorptivity of the surgical tool, the degree of scattering of radiation, or the beam hardening. The noise N(x, y) may be derived by a predetermined simulation and may be stored in the storage 13. In addition, the noise N(x, y) is included in the combination parameters.

$$C0(x,y)=G1(x,y)-w1\cdot G2(x,y)+N(x,y) \qquad (2)$$

In this embodiment, the combination unit 24 acquires a plurality of second radiographic images G2 by capturing the images of the gauze 40 rolled in different ways in order to train the discriminator, which will be described below, and changes the combination position of the second radiographic image G2 in the first radiographic image G1 or changes the combination parameters to generate a plurality of composite images C0. The composite image C0 may be generated using the plurality of first radiographic images G1.

The learning unit 25 trains the discriminator 30 so as to discriminate a surgical tool region in the input radiographic image, using a learning image including the plurality of composite images C0 and correct answer data in which the surgical tool region in the composite image C0 is specified. In addition, the correct answer data may be generated by a manual operation while viewing the composite image C0. A machine learning model can be used as the discriminator 30. One example of the machine learning model is a neural network model. Examples of the neural network model include a simple perceptron, a multilayer perceptron, a deep neural network, a convolutional neural network, a deep belief network, a recurrent neural network, and a stochastic neural network. In this embodiment, it is assumed that the convolutional neural network is used as the discriminator 30.

In a case in which the composite image C0 is input, the discriminator 30 is trained so as to output the probability that each pixel of the composite image C0 will be the surgical tool region. A region consisting of pixels with the probability which has been output from the discriminator 30 and is equal to or higher than a predetermined threshold value is the surgical tool region. The learning unit 25 inputs the composite image C0 to the discriminator 30 and directs the discriminator 30 to output the probability of being the surgical tool region. Then, the difference between the region consisting of the pixels having the probability which has been output from the discriminator 30 and is equal to or higher than the predetermined threshold value and a region represented by the correct answer data is derived as a loss. Then, the discriminator 30 is trained on the basis of the loss. Specifically, for example, a kernel coefficient in the convolutional neural network and a weight for the connection of neural networks are derived so as to reduce the loss. The learning unit 25 repeats learning until the loss is equal to or less than a predetermined threshold value. In this way, the discriminator 30 is trained such that a high probability equal to or greater than the predetermined threshold value is output for the surgical tool region included in the input radiographic image and the surgical tool region included in the input radiographic image is extracted.

The trained discriminator 30 is applied to the detection unit 22. In a case in which the target radiographic image G0 is input to the detection unit 22, the detection unit 22 directs the discriminator 30 to extract the surgical tool region included in the radiographic image G0, thereby detecting the surgical tool region.

Figure 7:
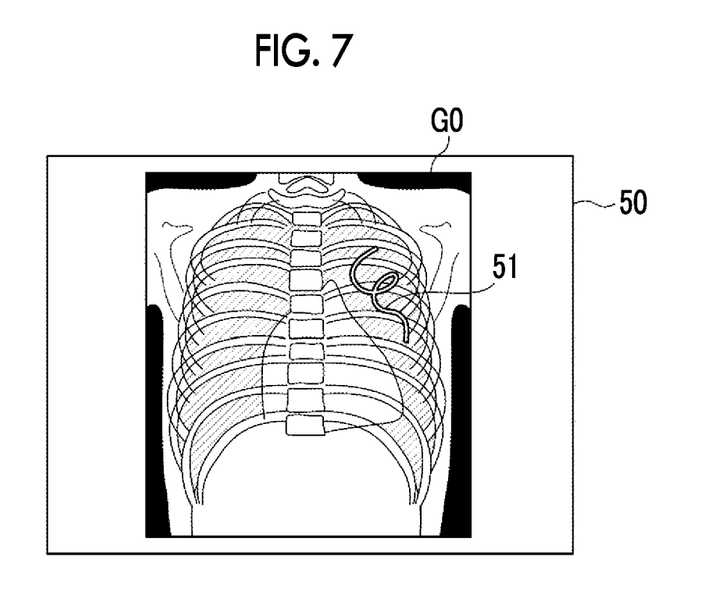
FIG. 7 is a diagram illustrating a radiographic image display screen.

The display control unit 23 displays the radiographic image G0 on the display unit 6 such that the surgical tool region detected from the radiographic image G0 by the detection unit 22 is highlighted. FIG. 7 is a diagram illustrating a radiographic image display screen. As illustrated in FIG. 7, the radiographic image G0 is displayed on a display screen 50 and the surgical tool region is highlighted by putting a mask 51 to the surgical tool region included in the radiographic image G0. The mask 51 is illustrated in white in FIG. 7. However, the mask 51 may be colored. Instead of putting the mask 51, a mark, such as an arrow or an asterisk, may be put in the vicinity of the surgical tool region to highlight the surgical tool region.

Figure 8:
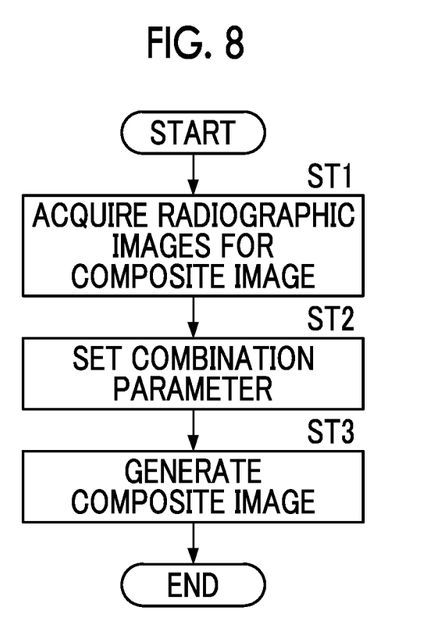
FIG. 8 is a flowchart illustrating a composite image generation process according to this embodiment.

Next, a process performed in this embodiment will be described. FIG. 8 is a flowchart illustrating a composite image generation process performed in this embodiment. First, the image acquisition unit 21 acquires the first radiographic image G1 and the second radiographic image G2 indicating the surgical tool which are used to generate the composite image C0 (the acquisition of radiographic images for a composite image; Step ST1). Then, the combination unit 24 sets combination parameters for the first radiographic image G1 and the second radiographic image G2 (Step ST2) and combines the first radiographic image G1 and the second radiographic image G2 according to the combination parameters to generate the composite image C0 (Step ST3). Then, the process ends.

Figure 9:
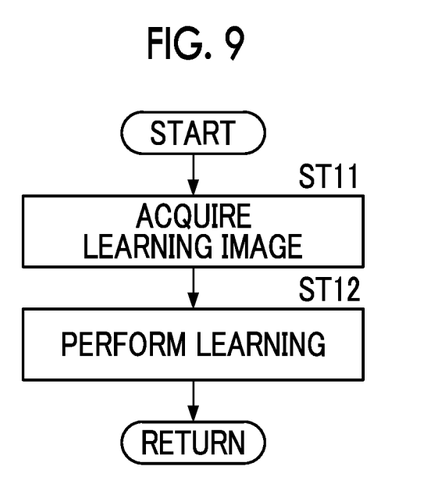
FIG. 9 is a flowchart illustrating a learning process according to this embodiment.

Next, a learning process according to this embodiment will be described. FIG. 9 is a flowchart illustrating the learning process performed in this embodiment. The learning unit 25 acquires a learning image consisting of the composite image C0 and correct answer data (Step ST11), inputs the learning image to the discriminator 30, acquires the extraction result of a surgical tool region, trains the discriminator 30 using the loss based on the difference from the correct answer data (Step ST12), and returns to Step ST11. Then, the learning unit 25 repeats the process in Steps ST11 and ST12 until the loss reaches a predetermined threshold value and ends the learning. The learning unit 25 may repeat the learning a predetermined number of times and end the learning.

Figure 10:
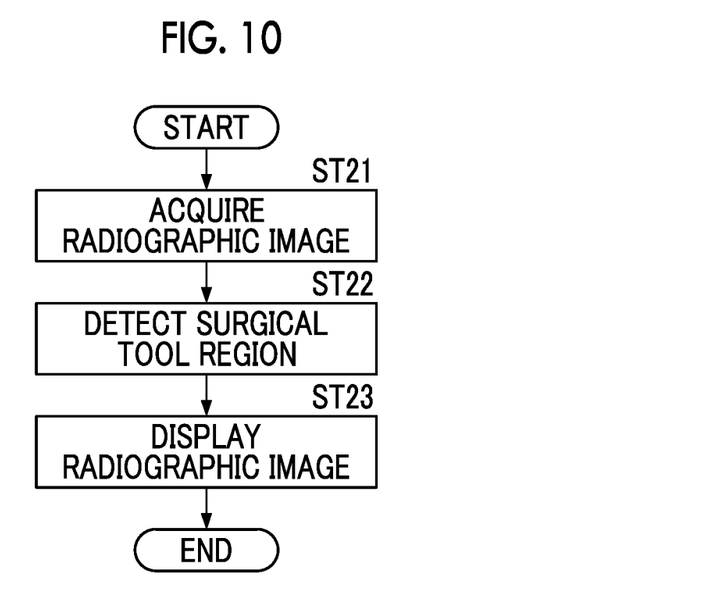
FIG. 10 is a flowchart illustrating a detection process according to this embodiment.

Next, a surgical tool region detection process according to this embodiment will be described. FIG. 10 is a flowchart illustrating the detection process performed in this embodiment. The image acquisition unit 21 acquires the radiographic image G0 as a detection target (Step ST21) and the detection unit 22 detects a surgical tool region from the radiographic image G0 (Step ST22). Then, the display control unit 23 displays the radiographic image G0 in which the surgical tool region has been highlighted on the display unit 6 (Step ST23). Then, the process ends.

As described above, in this embodiment, the detection unit 22 comprises the discriminator 30 that has been trained so as to discriminate the surgical tool region from the input radiographic image on the basis of training data consisting of the composite image C0 generated by combining the first radiographic image G1 and the second radiographic image G2 indicating the surgical tool and correct answer data indicating the surgical tool region in the composite image C0. Then, the discriminator 30 discriminates the surgical tool region in the input radiographic image G0 to detect the surgical tool region. Therefore, according to this embodiment, it is possible to reliably check whether or not a surgical tool remains in the body of the patient with reference to the detection result. As a result, according to this embodiment, it is possible to reliably prevent a surgical tool from remaining in the body of the patient after surgery.

In contrast, since the radiographic image which includes the surgical tool and is necessary for training the discriminator 30 is extremely rare, it is difficult to collect a large number of radiographic images for training the discriminator 30. In this embodiment, the discriminator 30 is trained by using the composite image C0 generated by combining the first radiographic image G1 and the second radiographic image G2 indicating the surgical tool. Therefore, it is possible to prepare a sufficient number of composite images C0. As a result, it is possible to construct the discriminator 30 with high surgical tool detection accuracy.

In the above-described embodiment, the gauze 40 as a surgical tool is a detection target. However, the present disclosure is not limited thereto. Any surgical tool used in surgery, such as a scalpel, scissors, a drain, a needle, a thread, or forceps, can be used as the detection target. In this case, the second radiographic image G2 including the surgical tool which is used to generate the composite image C0 may be acquired by capturing the image of a target surgical tool. Further, the discriminator 30 may be trained so as to discriminate the target surgical tool. The discriminator 30 is trained so as to detect a plurality of channels, which makes it possible to construct the discriminator 30 so as to discriminate not only one kind of surgical tool but also a plurality of kinds of surgical tools.

In addition, in the above-described embodiment, the radiation is not particularly limited. For example, α-rays and γ-rays other than X-rays can be applied.

In the above-described embodiment, for example, the following various processors can be used as a hardware structure of processing units performing various processes, such as the image acquisition unit 21, the detection unit 22, the display control unit 23, the combination unit 24, and the learning unit 25. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In such fashion, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiographic image processing apparatus comprising at least one processor, wherein the processor is configured to:
   discriminate the surgical tool region in the input radiographic image using a discriminator to detect the surgical tool region,
   wherein the discriminator has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image.

2. The radiographic image processing apparatus according to claim 1, wherein the processor is further configured to display the radiographic image on a display such that the surgical tool region detected in the radiographic image is highlighted.

3. The radiographic image processing apparatus according to claim 1, wherein the processor is further configured to combine the first radiographic image and the second radiographic image using a combination parameter corresponding to characteristics of the first radiographic image and the surgical tool to generate the composite image.

4. The radiographic image processing apparatus according to claim 3,
   wherein the processor is further configured to set the combination parameter according to at least one of radiation absorptivity of the surgical tool, a degree of scattering of radiation in the first radiographic image, beam hardening in the first radiographic image, or noise corresponding to imaging conditions of the first radiographic image.

5. The radiographic image processing apparatus according to claim 1,
   wherein the surgical tool includes at least one of gauze, a scalpel, scissors, a drain, a needle, a thread, or forceps.

6. The radiographic image processing apparatus according to claim 5,
   wherein at least a portion of the gauze includes a radiation absorbing thread.

7. The radiographic image processing apparatus according to claim 6, wherein the processor is further configured to train the discriminator, using a learning image consisting of the composite image and correct answer data in which a position of the surgical tool in the composite image is specified.

8. A radiographic image processing method performed in a radiographic image processing apparatus comprising a discriminator that has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image, the method comprising:

discriminating the surgical tool region in the input radiographic image using the discriminator to detect the surgical tool region.

9. A non-transitory computer-readable storage medium that stores a radiographic image processing program that causes a computer to perform a radiographic image processing method in a radiographic image processing apparatus comprising a discriminator that has been trained so as to discriminate a surgical tool region in an input radiographic image, on the basis of training data which consists of a composite image acquired by combining a first radiographic image including a human body and a second radiographic image including a surgical tool and correct answer data indicating the surgical tool region in the composite image, the program causing the computer to perform:

discriminating the surgical tool region in the input radiographic image to detect the surgical tool region.

* * * * *